US010921308B2

(12) United States Patent
Leblanc

(10) Patent No.: US 10,921,308 B2
(45) Date of Patent: Feb. 16, 2021

(54) ION SELECTIVE FIBER SENSORS FOR DETERMINING THE WATER CUT IN WELLBORE-RELATED FLUIDS

(71) Applicant: Halliburton Energy Services, Inc., Houston, TX (US)

(72) Inventor: Michel Joseph Leblanc, Houston, TX (US)

(73) Assignee: HALLIBURTON ENERGY SERVICES INC., Houston, TX (US)

( * ) Notice: Subject to any disclaimer, the term of this patent is extended or adjusted under 35 U.S.C. 154(b) by 278 days.

(21) Appl. No.: 15/768,515

(22) PCT Filed: Feb. 2, 2016

(86) PCT No.: PCT/US2016/016181
§ 371 (c)(1),
(2) Date: Apr. 13, 2018

(87) PCT Pub. No.: WO2017/135932
PCT Pub. Date: Aug. 10, 2017

(65) Prior Publication Data
US 2018/0299423 A1    Oct. 18, 2018

(51) Int. Cl.
*G01N 33/28* (2006.01)
(52) U.S. Cl.
CPC .................. *G01N 33/2847* (2013.01)
(58) Field of Classification Search
CPC ... G01N 33/2847; E21B 47/135; E21B 49/08; E21B 49/0875
See application file for complete search history.

(56) References Cited

U.S. PATENT DOCUMENTS

| 6,233,746 | B1 | 5/2001 | Skinner |
| 7,864,321 | B2 | 1/2011 | Caron et al. |

(Continued)

FOREIGN PATENT DOCUMENTS

| WO | WO-98/57030 A1 | 12/1998 |
| WO | WO-2009/082213 A1 | 7/2009 |

(Continued)

OTHER PUBLICATIONS

Bakker et al., "Carrier-Based Ion-Selective Electrodes and Bulk Optodes. 1. General Characteristics," Chem Rev. 1997, pp. 3083-3132.

(Continued)

*Primary Examiner* — Samuel P Siefke
(74) *Attorney, Agent, or Firm* — McGuirewoods, LLP

(57) ABSTRACT

The water cut of a fluid used or produced in conjunction with wellbore operations may be measured or otherwise estimated using an ion selective fiber sensor. For example, a method may include flowing a fluid comprising an aqueous phase and an oleaginous phase through a sensor; contacting an ion selective fiber positioned in the sensor with the fluid, wherein the ion selective fiber has an intrinsic time constant ($\tau_0$) associated with an intrinsic color change of the ion selective fiber in response to contact with the aqueous phase; measuring a color change of the ion selective fiber in response to contact with the fluid as a function of time; deriving an effective time constant ($\tau_{eff}$) for the color change of the ion selective fiber in response to contact with the fluid; and calculating a water cut (Y) in the fluid based on Y=

$$Y = \frac{\tau_0}{\tau_{eff}}. \tag{A}$$

8 Claims, 5 Drawing Sheets

(56) References Cited

U.S. PATENT DOCUMENTS

| 8,120,774 | B2 | 2/2012 | Fougeres et al. |
| 8,831,388 | B2 | 9/2014 | Boersma et al. |
| 2007/0193351 | A1 | 8/2007 | DiFoggio |
| 2009/0166520 | A1 | 7/2009 | Tuli et al. |
| 2014/0172302 | A1 | 6/2014 | Kalia et al. |

FOREIGN PATENT DOCUMENTS

| WO | WO-2009/084954 A2 | 7/2009 |
| WO | WO-2010/074569 A2 | 7/2010 |
| WO | WO-2014/099055 A1 | 6/2014 |

OTHER PUBLICATIONS

Boersma et al., "Fiber Bragg Distributed Chemical Sensor," IEEE, 2011, 4 pages.
Buhlmann et al., "Carrier-Based Ion-Selective Electrodes and Bulk Optodes. 2. Ionophores for Potentiometric and Optical Sensors," Chem Rev. 1998, pp. 1593-1687.
Mistlberger et al., "Ionophore-Based Optical Sensors," Annu. Rev. Anal. Chem., 2014, 7:483-512.
Ramos et al., "Oblique-Tip Fiber-Optic Sensors for Multiphase Fluid Discrimination," Journal of Lightwave Technology, Aug. 1999, vol. 17, No. 8, pp. 1392-1400.
International Search Report and Written Opinion from PCT/US2016/016181, dated Oct. 12, 2016, 11 pages.

ION SELECTIVE FIBER SENSORS FOR DETERMINING THE WATER CUT IN WELLBORE-RELATED FLUIDS

BACKGROUND

The present application relates to measuring the water cut of a fluid used or produced in conjunction with wellbore operations.

As used herein, the term "water cut" refers to the ratio of the volume of water produced relative to the volume of the total produced liquids. Globally, oil wells produce about 220 million barrels of water per day (BWPD), which is roughly three barrels of water for every barrel of oil. In older fields, the water cut may be 0.95 or higher. Managing produced water can be a great challenge for operators.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1:
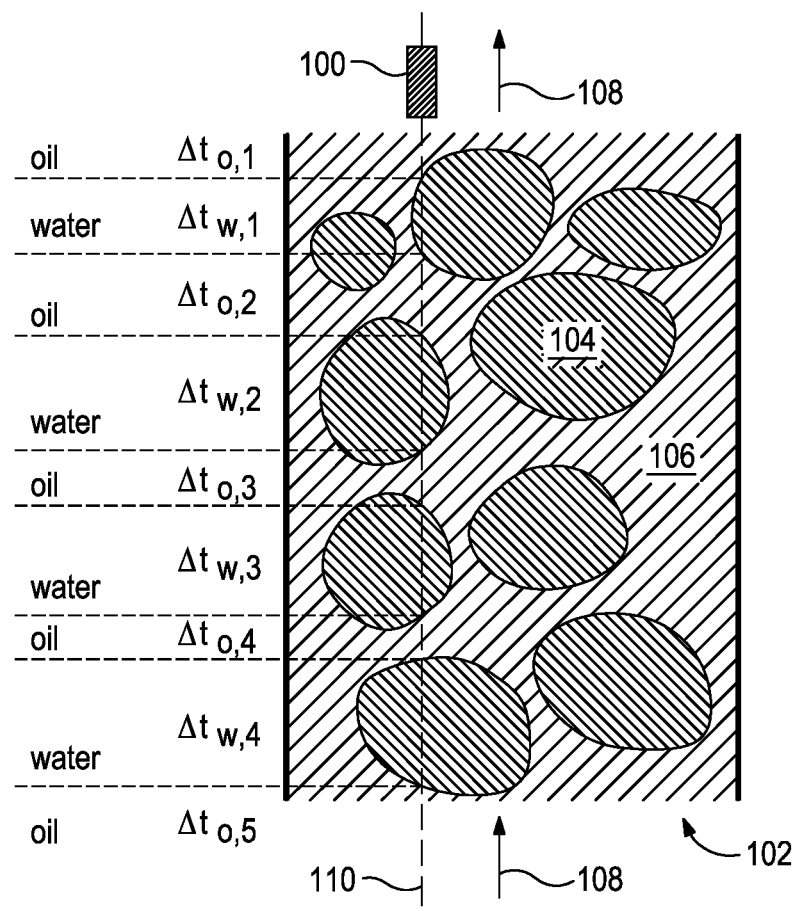
FIG. 1 provides an illustrative diagram of an ion selective fiber being exposed to a multi-phase fluid having an aqueous phase and an oleaginous phase flowing in a direction.

The present application relates to measuring the water cut of a fluid used or produced in conjunction with wellbore operations. More specifically, the relative amount of a water phase (also referred to herein as "an aqueous phase") in a multi-phase fluid may be measured or otherwise estimated using an ion selective fiber sensor.

An ion selective (ISF) is a fiber designed to change in optical characteristics when exposed to the presence of specific ions in surrounding aqueous fluid. A typical ISF includes a polymeric membrane containing chromo-ionophores. Chromo-ionophores are a class of molecules that bond to an ion, and when it does so, changes color, thereby changing its spectral absorption characteristics. A chromo-ionophore (dye) that is sensitive to protons (H+ ions) is common, since these are well-developed molecules used to measure pH. To render the membrane sensitive to other ions like sodium or potassium ions, another ionophore is also used in conjunction with the chromo-ionophore. The additional ionophore may bond (ligate) to the target ion and be optically unresponsive to the interrogation light. In order for the ionophore to ligate with the other ions, one or more proton from the chromo-ionophore needs to be released to the solution, so that the total charge of the membrane remains neutral. This interaction thus allows the optical response of a proton-sensitive dye (the chromo-ionophore) to be used for the measurement of other ions, as determined by the selectivity of the ionophores used. In some cases, other ionic-sites that do not participate in the ion-exchange but are there to balance the total charge of the membrane (to keep it neutral) may be used. There is a large variety of material selection and ionic interaction schemes that can be used to generate the optical response to ions.

As used herein, the term "color change" and any grammatical equivalent thereof refer to wavelength changes, intensity changes (increases or decreases), or a combination thereof, which may occur at any wavelength along the electromagnetic spectrum, and not necessarily in the visible region.

Because the ions traverse the membrane and undergo ligation, the response time of the ion selective fiber is not instantaneous and depends on the thickness of the membrane and the concentration and composition of the chromo-ionophores and ionophores. Given sufficient interaction time between the aqueous fluid and the ion selective fiber to reach equilibrium, the total color change of the ion selective fiber relates to the ionic concentration of the aqueous fluid and is, to some degree, dependent on pressure and temperature. The rate of the response time (i.e., color change as a function of time) when the ion selective fiber is in an aqueous fluid is referred to herein as an intrinsic time constant ($\tau_0$). The time constant can be further tailored by the use of a low-permeability layer surrounding the ion selective fiber that slows down the ionic exchange between the membrane and the surrounding solution.

Exemplary membrane compositions may include, but are not limited to, plasticized polyvinyl chloride (PVC) containing a chromo-ionophore/indicator (e.g., a lipophilic pH indicator), an ion-selective ionophore, ionic sites, and any combination thereof.

Exemplary ionophore may include, but are not limited to, ETH 1001 (a $Ca^{2+}$-selective ionophore, available from Sigma-Aldrich), calimycin (a $Ca^{2+}$-selective ionophore, available from Sigma-Aldrich), ETH 1117 (a $Mg^{2+}$-selective ionophore, available from Sigma-Aldrich), ETH 227 (a $Na^+$-selective ionophore, available from Sigma-Aldrich), ETH 4120 (a $Na^+$-selective ionophore, available from Sigma-Aldrich), valinomycin (a $K^+$-selective ionophore), BME 44 (a $K^+$-selective ionophore), 6,6-dibenzyl-14-crown-4 (a $Li^+$-selective ionophore), and any combination thereof.

The ionic site of the ionophore may be provided by, for example, sodium tetrakis[3,5-bis(trifluoromethyl)phenyl] borate (NaTFPB).

The low-permeability layer surrounding the ion selective fiber used to adjust the time constant may be composed of materials that include, but are not limited to, polyimide, NAFION™ (a sulfonated tetrafluoroethylene based fluoropolymer-copolymer), and any combination thereof.

FIG. 1 provides an illustrative diagram of an ion selective fiber 100 being exposed to a multi-phase fluid 102 having an aqueous phase 104 and an oleaginous phase 106 flowing in direction 108. While the multi-phase fluid 102 is depicted as a water-in-oil emulsion, the same principles described herein may apply to an oil-in-water emulsion, without departing from the scope of the present disclosure.

As the multi-phase fluid 102 flows over the ion selective fiber 100, the ion selective fiber 100 is exposed periodically to the aqueous phase 104 or the oleaginous phase 106. For illustrative purposes, it is assumed that the ion selective fiber 100 is exposed to the multi-phase fluid 102 flowing along a flow path 110 that aligns with the ion selective fiber 100, which allows the ion selective fiber 100 to be exposed to the aqueous phase 104 and the oleaginous phase 106 at various times, represented in FIG. 1 as $\Delta t_{w,i}$ and $\Delta t_{o,j}$, respectively. Accordingly, the total time (t) the ion selective fiber 100 is exposed to the multi-phase fluid 102 is represented by Equation 1.

$$t = \Sigma_i \Delta t_{w,i} + \Sigma_j \Delta t_{o,j} \qquad \text{Equation 1}$$

The ion selective fiber 100 response will be only to the aqueous phase 106, which provides for a sensor response ($X_{meas}$) according to Equation 2.

$$X_{meas} = X_\infty (1 - e^{-t_{eff}/\tau_0}) \qquad \text{Equation 2}$$

where: $X_\infty$ is the sensor response at equilibrium
$t_{eff}$ is $\Sigma_i \Delta t_{w,i}$ For Equation 2 to be valid, the distribution of ligated ions in proximity to the fiber portion of the ion selective fiber 100 should not vary appreciably during each time $\Delta t_{o,j}$ the ion selective fiber 100 is exposed to the oleaginous phase 106. This will be true (1) when the times $\Delta t_{o,j}$ are of short compared to the original time constant $\tau_0$, or (2) when a low permeability layer is used such that the concentration of ligated ions within the membrane of the ion selective fiber 100 is uniform.

The sensor response may be (1) a measured attenuation or a fluorescence level at a single wavelength, (2) from the weighted response of such measurements obtained at several wavelengths, or (3) may involve the calculation of one or more ratios of the optical response at several wavelengths. For the purpose of the present application, the optical sensor response needs only to be directly related to the concentration of ligated ions of interest in the part of the coating that is optically interrogated by the evanescent wave. The water cut (or aqueous phase proportion) (Y) of the multi-phase fluid 102 may be given by Equation 3, where Y=1 would be a single-phase aqueous fluid.

$$Y = \frac{V_w}{V_w + V_o} \qquad \text{Equation 3}$$

where: $V_w$ is the volume of the aqueous phase 104 in the multi-phase fluid 102
$V_o$ is the volume of the oleaginous phase 106 in the multi-phase fluid 102

Assuming (1) constant fluid velocity during the measurement time t and (2) the fluid along line 110 (FIG. 1) passing through the sensor 100 has an oil/water distribution representative of the whole flowing fluid, then, the interaction times with each phase are proportional to the volumes of those fluids, which provides for Equation 4.

$$Y = \frac{V_w}{V_w + V_o} = \frac{\sum_i \Delta t_{w,i}}{\sum_i \Delta t_{w,i} + \sum_j \Delta t_{o,j}} \qquad \text{Equation 4}$$

Using Equations 1 and 3 and $t_{eff} = \Sigma_i \Delta t_{w,i}$, as defined above, Equation 5 can be derived as:

$$Y = \frac{t_{eff}}{t} \qquad \text{Equation 5}$$

Then, Equation 2 can be rewritten using the foregoing equations as illustrated in Equations 6.

$$X_{meas} = X_\infty (1 - e^{-Yt/\tau_0}) \qquad \text{Equation 6}$$

$$X_{meas} = X_\infty \left(1 - e^{-t/(\frac{\tau_0}{Y})}\right)$$

$$X_{meas} = X_\infty \left(1 - e^{-t/\tau_{eff}}\right)$$

$$\tau_{eff} = \frac{\tau_0}{Y}$$

where:

Therefore, the color change of the ion selective fiber 100 may be measured as a function of time to obtain $\tau_{eff}$ (the effective time constant) and to calculate Y according to Equation 7.

$$Y = \frac{\tau_0}{\tau_{eff}} \qquad \text{Equation 7}$$

In other words, from the knowledge of the time constant of the sensor in the water-based solution $\tau_0$ (the original time constant) and the measured time constant $\tau_{eff}$ (from exposure to the oil-water mixture), the relative amount of a water phase may be determined.

Generally, the composition and configuration of the ion selective fiber 100 should be chosen to provide for $\tau_0$ to be reasonably long to be able to effectively differentiate $\tau_0$ and $\tau_{eff}$ but within the timeframe of the exposure to the multi-phase fluid 102 so that a color change may occur. Among other variables, the selection of the outer layer, with particular attention to the permeability of this layer to the ions undergoing exchange with the aqueous phase, may be important for achieving this function. In some instances, multiple ion selective fibers with different $\tau_0$ or multiple ion selective fibers sensors with different $\tau_0$ may be implemented when the ion concentrations of the aqueous phase 104 are unknown.

When comparing $\tau_{eff}$ and $\tau_0$ according to Equation 7, the conditions at the sensor (e.g., temperature, pressure, salinity, etc.) should be the same or substantially similar for $\tau_0$ and $\tau_{eff}$. Substantially similar conditions would provide for less than a 5% change in $\tau_0$. The conditions at the sensor having the ion selective fiber 100 (e.g., the salinity of the aqueous phase 104 in the multi-phase fluid 102) may be known, measured, or estimated so that the appropriate $\tau_0$ is used in Equation 7 to calculate Y. Here the term "salinity" is used as a generic term to indicate the value of the term $X_\infty$ which is needed for the proper fitting of Equation 6 for the determination of $\tau_{eff}$, leading to Y via Equation 7. We note here that the fitting of Equation 6 to the measured response $X_{meas}(t)$ using $\tau_{eff}$ as the parameter may be done, for example, by a least square fitting method or any other similar mathematical fitting algorithm.

Measuring the salinity ($X_\infty$) of the aqueous phase 104 may be achieved with any suitable analysis method including, but not limited to, electrical conductivity, total dissolved solids, elemental analysis (e.g., with inductively coupled plasma-atomic absorption or -mass spectroscopy), titration, or a combination thereof. Salinity measurements may be performed using a sensor at the surface, downhole, or a combination thereof. In some instances, in combination with or apart from the foregoing methods, a separate reference ion selective fiber may be used to measure or derive the salinity of the aqueous phase of the multiphase fluid. Such methods may be advantageous since the reference ion selective fiber may be placed in close proximity to the ion selective fiber used in conjunction with measuring or deriving Y, which, when the sensors including ion selective fibers are located downhole, may provide a more accurate sampling of the aqueous phase in the multi-phase fluid. Additionally, ion selective fibers may be selective to only some of the ions in the aqueous phase in the multi-phase fluid, while some foregoing methods are not selective and rather provide a salinity based on all ions. That is, $X_\infty$ may be either measured directly or inferred from the measurements and known properties of the fluid.

When using a reference ion selective fiber to measure or derive the $X_\infty$ of the aqueous phase of the multiphase fluid, the corresponding $\tau_0$ of the reference measurement should be sufficiently short so that the reference ion selective fiber approaches equilibrium (e.g., less than a 5% color change over 1 min) with the aqueous phase of the multiphase fluid rapidly. Once equilibrium is approached, the total color change of the reference ion selective fiber may be measured and used to derive the $X_\infty$ of the aqueous phase.

If a separate measurement of ion concentration in the aqueous phase is not available, the same sensor as used for the water cut measurement may be used to determine $X_\infty$ by collecting data over a sufficiently long period so that equilibrium is reached because $X_\infty$ is the asymptotic value $X_{meas}(t)$. As would be recognized by one of skill in the art, using the same sensor to determine $X_\infty$ assumes that $X_\infty$ is within the measurable range of the sensor 100 (i.e., sensor 100 is not saturated in a fluid with salinity $X_\infty$).

Figure 2:
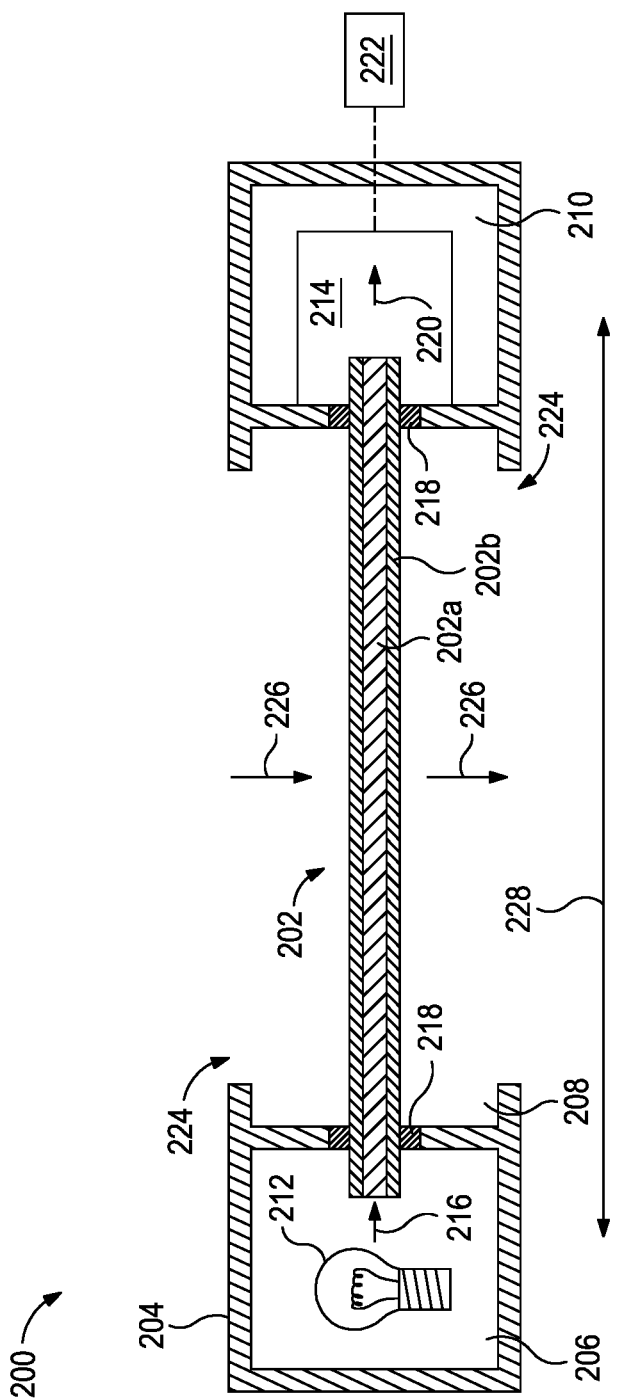
FIG. 2 provides a cross-sectional diagram of an exemplary sensor with an ion selective fiber.

FIG. 2 provides a cross-sectional diagram (not to scale) of an exemplary sensor 200 with an ion selective fiber 202, according to one or more embodiments. The sensor 200 includes a housing 204 with three compartments 206, 208, 210 that respectively contain a light source 212, the ion selective fiber 202, and a detector 214. The illustrated compartments 206, 208, 210 and components contained therein are configured such that light 216 emitted by the light source 212 travels along the length 228 of the ion selective fiber 202 in the compartment 208. The ion selective fiber 202 includes a fiber 202a with a membrane 202b. As the light 216 travels down the fiber 202a, the light 216 interacts with the membrane 202b via a total internal reflection mechanism. As a result, light 220 that exits the fiber 202b at the detector 214 relates to the color change of the membrane 202b caused by the membrane 202b/fluid 226 interaction. The light 220 received by the detector 214 may be analyzed for a color change with a processor 222 or another type of computing device communicably coupled to the detector 214. The processor 222 may be included in the sensor 200, for example, or may alternatively be remotely located from, but nonetheless communicably coupled to, the sensor 200. Membrane 202b may be composed of one or several layers, with different compositions, as needed to obtain the effective time constant and environmental resistance required for the application.

The compartment 208 that houses the ion selective fiber 202 may have opposing ports 224 defined in the housing 204 to allow a fluid being analyzed to flow therethrough, for example, in the general direction of arrows 226. The ion selective fiber 202 may be secured within the compartment 208 so as to extend between the other compartments 206, 210 housing the light source 212 and the detector 214. As illustrated, a seal 218 is used secure the ion selective fiber 202 in place. Other mechanisms may be utilized including clamps or other securing components (not illustrated).

Exemplary light sources suitable for use in the sensors described herein may include, but are not limited to, bulbs, light emitting diodes, semiconductor lasers, or the like in any suitable wavelength for the membrane being implemented.

The ion selective fiber may be implemented in a plurality of different configurations. For example, as illustrated in FIG. 2, a single fiber 202 is used in the sensor. Alternatively, a bundle or braid of ion selective fibers may be used. In some instances, the entire ion selective fiber may not be sensitive to ion concentrations (not shown). For example, the ion selective fiber may comprise one or more sensing lengths coupled to one or more insensitive lengths. Such configurations may be useful for lead-in of the interrogating light and lead-out of the sensor signal, which may be implemented in alternative embodiments to those described in FIGS. 3-4 below. Further, as illustrate in FIG. 2, the ion selective fiber 202 is bare and fully in contact with the fluid 226. Alternatively, the fiber 202, a bundle of fibers, or a braid of fibers may have a permeable sheath, for example, a perforated tubing.

Figure 3:
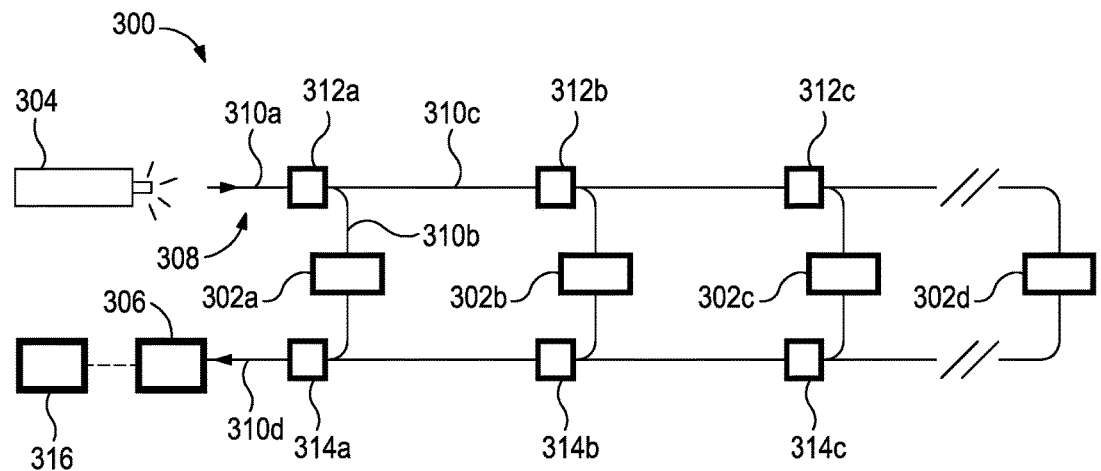
FIG. 3 provides a diagram of an exemplary sensor configuration for implementing a plurality of ion selective fibers with a single light source and a single detector.

FIG. 3 provides a diagram (not to scale) of an exemplary sensor configuration 300 for implementing a plurality of ion selective fibers 302 with a single pulsed light source 304 (e.g., a laser) and a single detector 306. The light source 304 is pulsed and coupled to a fiber optic system 308. The illustrated fiber optic system 308 includes fiber optic cables 310, light splitters 312, and light combiners 314. The light pulse begins by travelling down a fiber optic cable 310a until it reaches a light splitter 312a that splits the light such that a portion of the light is transmitted via a fiber optic cable 310b to an ion selective fiber 302a and the remaining light is transmitted via another fiber optic cable 310c to second light splitter 312b. The light received by the second light splitter 312b is similarly split so that a portion of the light received is transmitted to a second ion selective fiber 302b. The sensor configuration 300 includes as many light splitters 312 as needed for transmitting light to the plurality of ion selective fibers 302.

Each portion of light having interacted with the ion selective fibers 302 is then transmitted to a corresponding light combiner 314 that combines the light channels from the corresponding ion selective fiber 302 with the light channels from the ion selective fibers 302 located earlier in the fiber optic system 308. Because the light from the more distant sensors (e.g., sensor 302d) takes longer to travel to detector 306 compared to the light from the sensors closer to the detector (e.g., sensory 302a), the light from the different sensors will arrive at the detector 306 different times. Based on the arrival time of the light, it is possible to distinguish which sensor 302 is being interrogated. To avoid overlap in the pulses received from the various sensors, the pulse of light may be sufficiently short in duration, and a delay between successive pulses from the light source 304 be long enough to ensure that the pulse from the most distant sensor 302d reaches detector 306 before the next pulse from the closest sensor 302a reaches the detector 306. This technique is known as time-division multiplexing and is well understood in the art of fiber optic sensing.

For example, in the illustration of FIG. 3, light from second ion selective fiber 302b is transmitted to a light combiner 314b, which is combined with the light channels from ion selective fibers 302c, 302d located further in the fiber optic system 308. The resultant aggregated light pulse train is guided to the next light combiner 314a, which also receives light from the first ion selective fiber 302a and combines to two signals. The light combiner 314b transmits the combined light signal via a fiber optic cable 310d to the detector 306. The detector 306 may be coupled to a processor 316 for analyzing the light received by the detector 306.

Figure 4:
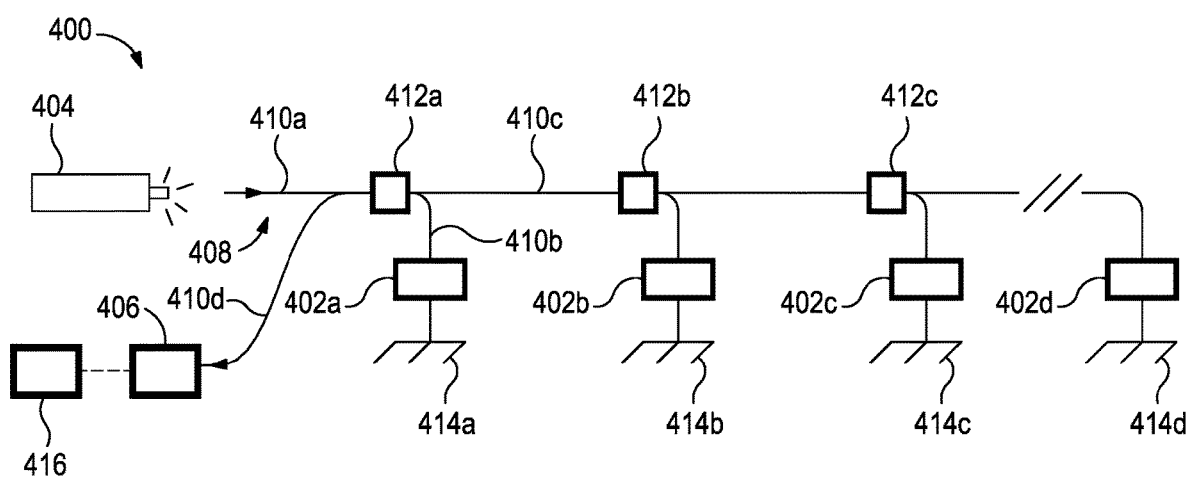
FIG. 4 provides a diagram of an alternate exemplary sensor configuration for implementing a plurality of ion selective fibers with a single light source and a single detector.

FIG. 4 provides a diagram (not to scale) of an alternate exemplary sensor configuration 400 for implementing a plurality of ion selective fibers 402 with a single light source 404 and a single detector 406. The light source 404, which is also pulsed, is coupled to a fiber optic system 408. The illustrated fiber optic system 408 includes fiber optic cables 410, light splitters/combiners 412, and mirrors 414. The light begins by travelling down a fiber optic cable 410a until it reaches a light splitter/combiner 412a that splits the light such that a portion of the light is transmitted via a fiber optic cable 410b to an ion selective fiber 402a and the remaining light is transmitted via another fiber optic cable 410c to second light splitter/combiner 412b. The light received by the second light splitter/combiner 412b is similarly split so that a portion of the light received is transmitted to a second ion selective fiber 402b. The sensor configuration 400 includes as many light splitters/combiners 412 as needed for transmitting light to the plurality of ion selective fibers 402.

The light having interacted with each of the ion selective fibers 402 is then reflected by a corresponding mirror 414, transmitted back through the ion selective fiber 402, and received by the fiber optic cable 410 that originally transmitted light to the ion selective fiber 402. For example, the light transmitted to the first ion selective fiber 402a via the fiber optic cable 410b traverses the first ion selective fiber 402a, reflects off of the mirror 414a, traverses the first ion selective fiber 402a again, and is transmitted to the first light splitter/combiner 412a. The light from the first ion selective fiber 402a received by the first light splitter/combiner 412a is combined with the light from the second light splitter/combiner 412b and transmitted via a fiber optic cable 410d to the detector 406 coupled to a processor 416. As described relative to FIG. 3, the different arrival times of the pulses from the various sensor locations allows the detector 406 and/or the processor 416 to distinguish between the light from the various sensors.

Each of the ion selective fibers 302,402 of FIGS. 3 and 4 may be the same or different within the individual sensor configurations 300,400. Further, the individual selective fibers 302,402 may be in housings or other fixtures that maintain the individual selective fibers' 302,402 position within the flow of the fluid. Further, the fiber optic cables 310,410 may have appropriate coverings or coatings for implementation of the sensors.

In alternative embodiments, sensors may be configured similar to FIG. 3 or 4 with more than one detector, more than one light source, or more than one of both the detector and the light source. The pulsed light source may be a semiconductor laser which is current-modulated, continuous wave semiconductor laser followed by an electro-optic or acousto optic modulator, a pulsed supercontinuum light source, or other pulsed light source as known in the art.

The sensing approach described herein uses measurements made before the chemical sensor reaches equilibrium with its surrounding solution. Without a method to refresh the sensor by reducing the amount of ligated ions that cause the color change, the sensor may have a limited lifetime for sensing. In some embodiments, the sensor may be configured in compositions and/or components to refresh the sensor by changing the equilibrium response of the sensor. As used herein, refresh does not necessarily mean that the equilibrium response is changed back to the original state before exposure to the chromo-ionophores and/or ionophores.

Refreshing may be achieved by exposing the ion selective fiber to light of a different wavelength than the interrogation wavelength. In these embodiments, the refreshing light source may be included in a sensor and otherwise operably coupled thereto for (1) de-ligating ions from the chromo-ionophores and/or ionophores, (2) desorbing the ions from the membrane, or (3) a combination thereof. Generally, such a light source is different than the light sources 212,312 used interrogate color changes to the ion selective fibers.

Alternatively or in combination with a refreshing light source, the sensor may be refreshed by flushing the sensor (or at least the ion selective fiber) with a cleaning solution that is void (or having very low concentration) of the target ion. Depending on the configuration and complexity of the sensor, flushing may be performed downhole or after the sensor is retrieved from the wellbore (e.g., at the surface of the well site).

In some instances, the sensor may be discarded and replaced with a new one for performing additional measurements of the relative amount of water phase in a fluid.

The sensors described herein with one or more ion selective fibers may be used in various locations along a hydrocarbon production system to measure, analyze, or otherwise estimate the water cut at the location of the sensors.

Figure 5:
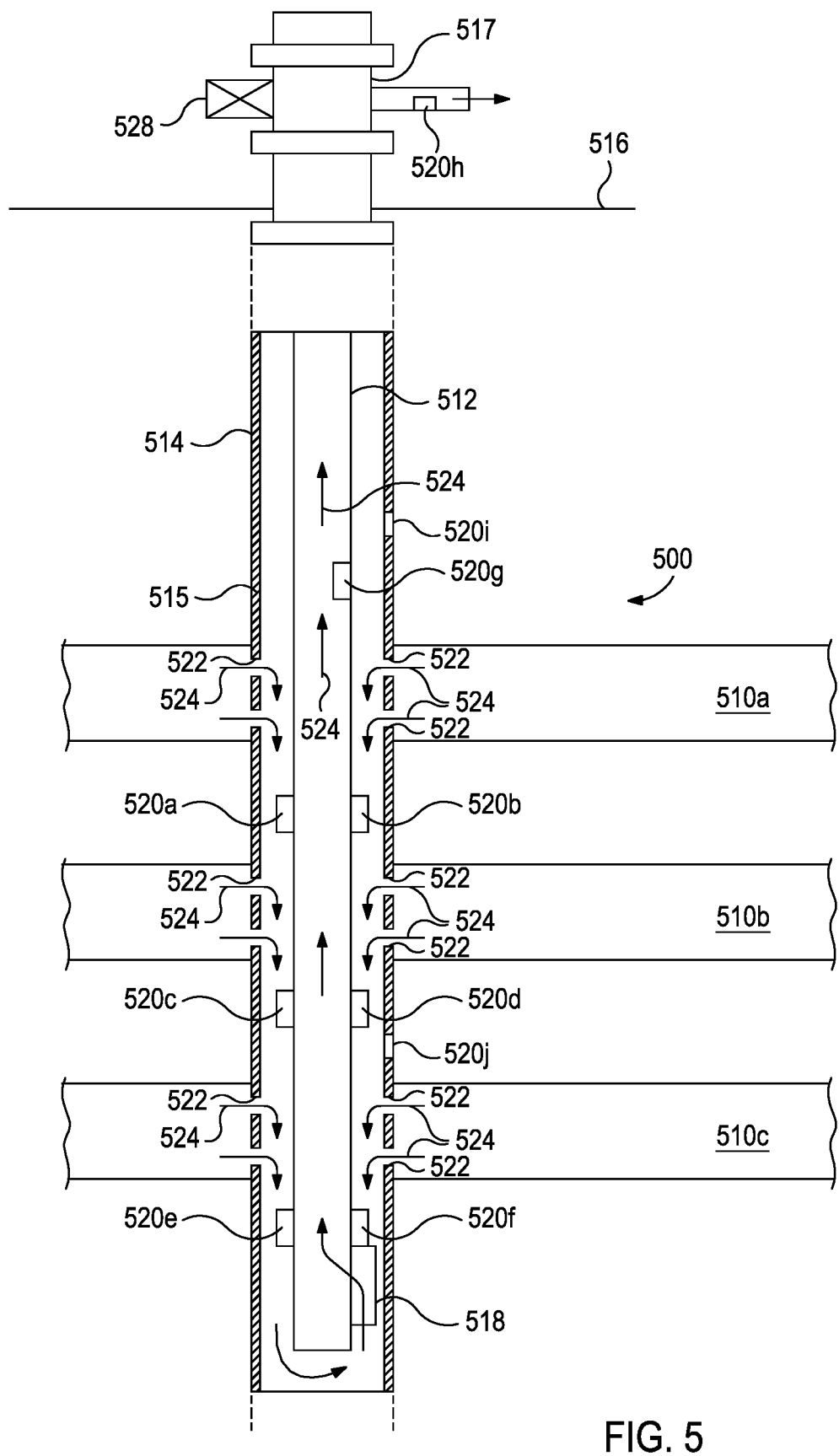
FIG. 5 illustrates a hydrocarbon production system with a plurality of sensors that each comprises at least one ion selective fiber.

FIG. 5 illustrates a hydrocarbon production system 500 with a plurality of sensors 520a-h that each comprises at least one ion selective fiber. The system 500 may include a tubular 512 disposed in a wellbore 514 that penetrates subterranean zones 510a, 510b, 510c, and the tubular 512 may be adapted to convey fluids from the subterranean zones 510a, 510b, 510c to a surface location 516 in the direction generally indicated by arrows 524. A downhole fluid lift system 518, operable to lift fluids towards the surface location 516, is at least partially disposed in the wellbore 514 and may be integrated into, coupled to, or otherwise associated with the tubular 512.

A wellhead 517 may be disposed proximal to the surface location 516. The wellhead 517 may be operatively coupled to a casing 515 that extends a substantial portion of the length of the wellbore 514 surface location towards the subterranean zones 510a, 510b, 510c. Each of the subterranean zones 510a, 510b, 510c may include part of a formation or multiple formations. In some instances, the casing 515 may terminate at or above one of the subterranean zones 510a, 510b, 510c, thereby leaving the wellbore 514 un-cased through lower subterranean zones 510a, 510b, 510c, which is commonly referred to as "open hole." In other instances, as illustrated, the casing 515 may extend through the subterranean zones 510a, 510b, 510c and may include apertures 522 either formed prior to installing the casing 515 or otherwise by downhole perforating operations to allow fluid communication between the interior of the wellbore 514 and the subterranean zones 510a, 510b, 510c. Some, all, or none of the casing 515 may be affixed to the adjacent ground material with a cement jacket or the like.

In the illustrated embodiment, wellbore 514 is a substantially vertical wellbore extending from surface location 516 to subterranean zones 510a, 510b, 510c. However, the systems and methods described herein can also be used with other wellbore configurations (e.g., deviated wellbores, horizontal wellbores, multilateral wellbores, and other configurations).

The tubular 512 may be an appropriate tubular completion member configured for transporting fluids. For example, the tubular 512 may be jointed production tubing, coiled tubing, production tubing, or similar pipe lengths. One or more sensors may be coupled or otherwise secured to the tubular 512 at various locations (illustrated as six sensors 520a-f coupled to the exterior of the tubular 512 and one sensor 520g coupled to the interior of the tubular 512). Further, one or more sensors may be coupled or otherwise secured to the casing 515 (illustrated as two sensors 520i-j) that interact with fluids inside the casing 515 and/or fluids behind the casing 515 (i.e., between the casing 515 and the wellbore 514).

Coupling to the tubular 512, the casing 515, or other components of the system may be by any suitable means including welding, brazing, adhering, threading, using one or more mechanical fasteners (i.e., screws, bolts, snap rings, pins, etc.), and the like.

In some instances, the tubular 512 may be located in the wellbore 514 to position one or more of the sensors 520a-f downstream of each subterranean zone 510a, 510b, 510c. More specifically, as illustrated, subterranean zone 510a is located upstream of subterranean zones 510b, 410c and all sensors 520a-h, subterranean zone 510b is downstream of subterranean zone 510a and sensors 520a-b and upstream of subterranean zone 510c and sensors 520c-h, and subterranean zone 510c is downstream of both subterranean zones 510a, 510b and sensors 520a-d and upstream of sensors 520e-h.

The water cut at each of the sensors 520a-f may be measured and thereby provide an indication of which, if any, of the subterranean zones 510a, 510b, 510c has a high water cut. In some instances, for example, if subterranean zone 510a has a first Y and subterranean zone 510b has a second Y (each as calculated as described herein), a remedial action may be taken when second Y>(first Y)*1.5 or second Y>(first*2 to reduce the flow through subterranean zone 510b, thereby reducing the water cut of the produced fluid at the wellhead 517. For example, packers with a flow bypass or chemical methods (e.g., swellable polymer diverters and sealants) may be used isolate and/or seal subterranean zone 510b from the fluid being produced. These remedial action criteria are given here for illustration purposes only and will depend on the particular situation and the goals of the operator of the well being monitored.

Also, illustrated are (1) a sensor 520g inside the tubular 512 for measuring the water cut of the fluid before it reaches the wellhead 517 and (2) a sensor 520h downstream of the wellhead 517 that may be useful in measuring the water cut before transporting the fluid to a pipeline, a tanker, a storage facility, a hydrocarbon/water separation equipment, or the like.

The system 500 may also further include a control system(s) 528 communicably coupled to various components of the system 500 (e.g., the downhole fluid lift system 518, the sensors 520a-h, and the like) and be capable of executing the mathematical algorithms, methods, and water cut analyses described herein. Control system 528 may be in proximity to the well, as shown here, or communicably placed remotely from the well, either by extending the fiber optic cables 310a/410a or by implementation of separate telemetry from a sub-system (interrogator, in place of 528) to a remote control system.

The control system(s) 528 and corresponding computer hardware used to implement the various illustrative blocks, modules, elements, components, methods, and algorithms described herein can include a processor (e.g., processors 222, 316, 416 of FIGS. 2-4) configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable programmable read only memory (EPROM)), registers, hard disks, removable disks, CD-ROMs, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

Embodiments described herein include, but are not limited to, Embodiment A, Embodiment B, and Embodiment C.

Embodiment A is a method that comprises: flowing a fluid comprising an aqueous phase and an oleaginous phase through a sensor; contacting an ion selective fiber positioned in the sensor with the fluid, wherein the ion selective fiber has an intrinsic time constant ($\tau_0$) associated with an intrinsic color change of the ion selective fiber in response to contact with the aqueous phase; measuring a color change of the ion selective fiber in response to contact with the fluid as a function of time; deriving an effective time constant ($\tau_{eff}$) for the color change of the ion selective fiber in response to contact with the fluid; and calculating a water cut (Y) in the fluid based on $$Y = \frac{\tau_0}{\tau_{eff}}.$$

Optionally, Embodiment A may include one or more of the following elements: Element 1: wherein the ion selective fiber comprises an outer layer as a diffusion barrier that increases $\tau_0$; Element 2: wherein the sensor further comprises a light source and the method further comprises: refreshing the ion selective fiber by exposing the ion selective fiber to light emitted from the light source; Element 3: Element 2 and wherein the fluid is a first fluid comprising a first aqueous phase and a first oleaginous phase, and wherein the method further comprises: contacting the ion selective fiber with a second fluid comprising a second aqueous phase and a second oleaginous phase after exposing the ion selective fiber to the light; measuring a second color change of the ion selective fiber in response to contact with the second fluid as a function of time; deriving a second effective time constant for the second color change of the ion selective fiber in response to contact with the second fluid; and calculating a second concentration of the second aqueous phase in the second fluid based on the second effective time constant and the intrinsic time constant; Element 4: Element 2 and wherein refreshing the ion selective fiber is conducted while the sensor is in a wellbore penetrating a subterranean formation; Element 5: wherein the fluid is a first fluid, and wherein the method further comprises: refreshing the ion selective fiber by exposing the ion selective fiber to a second fluid having a reduced concentration of a chromo-ionophore or an ionophore as compared to the first fluid; Element 6: Element 5 and wherein the first fluid comprises a first aqueous phase and a first oleaginous phase, and wherein the method further comprises: contacting the ion selective fiber with a second fluid comprising a second aqueous phase and a second oleaginous phase after exposing the ion selective fiber to the light; measuring a second color change of the ion selective fiber in response to contact with the second fluid as a function of time; deriving a second effective time constant for the second color change of the ion selective fiber in response to contact with the second fluid; and calculating a second concentration of the second aqueous phase in the second fluid based on the second effective time constant and the intrinsic time constant; Element 7: Element 5 and wherein refreshing the ion selective fiber is conducted while the sensor is in a wellbore penetrating a subterranean formation; Element 8: producing the fluid from a subterranean formation via a wellbore penetrating the subterranean formation, wherein the sensor is in the wellbore; and Element 9: Element 8 and wherein the subterranean formation comprises a first zone upstream of a second zone, and wherein the sensor is a first sensor at a first location along the wellbore downstream of the first zone and upstream of the second zone, the ion selective fiber is a first ion selective fiber, the color change is a first color change, the $\tau_{eff}$ is a first $\tau_{eff}$, and the Y is a first Y, and wherein the method further includes: contacting a second sensor with a fluid, wherein the second sensor is at a second location along the wellbore that is downstream of the first and second zones and comprises a second ion selective fiber that is same as the first ion selective fiber; measuring a second color change of the second ion selective fiber of the second sensor in response to contact with the fluid as a function of time; deriving a second $\tau_{eff}$ for the second color change; and calculating a second Y of the aqueous phase in the fluid at the second sensor based on the $$Y = \frac{\tau_0}{\tau_{eff}}$$

and the second $\tau_{eff}$. Exemplary combinations may include, but are not limited to, Elements 2 and 5 in combination and optionally in further combination with at least one of Elements 3, 4, 6, or 7; Elements 2, 5, and 8 in combination and optionally in further combination with at least one of Elements 3, 4, 6, 7, or 9; Elements 2 and 8 in combination and optionally in further combination with at least one of Elements 3, 4, or 9; Elements 5 and 8 in combination and optionally in further combination with at least one of Elements 6, 7, or 9; Element 1 in combination with any of the foregoing combinations; and Element 1 in combination with one or more of Elements 2-9.

Embodiment B is a method that comprises: contacting a first ion selective fiber and a second ion selective fiber with a fluid comprising an aqueous phase and an oleaginous phase, wherein the first and second ion selective fibers are different compositions; measuring a first color change of the first ion selective fiber as a function of time in response to contact with the fluid until the first color change of the first ion selective fiber approaches equilibrium; calculating a salinity of the aqueous fluid based on the first color change; calculating an intrinsic time constant ($\tau_0$) for a second color change of the second ion selective fiber as a function of time in response to contact the aqueous phase based on the salinity of the fluid; measuring the second color change in the second ion selective fiber as a function of time in response to contact with the fluid; deriving an effective time constant ($\tau_{eff}$) for the second color change of the second ion selective fiber as the function of time in response to contact with the fluid; and calculating a water cut (Y) of the aqueous phase in the fluid based on $$Y = \frac{\tau_0}{\tau_{eff}}.$$

Optionally, Embodiment B may include one or more of the following elements: Element 10: wherein the second ion selective fiber comprises an outer layer as a diffusion barrier that increases $\tau_0$; Element 11: wherein the sensor further comprises a light source and the method further comprises: refreshing the second ion selective fiber by exposing the second ion selective fiber to light emitted from the light source; Element 12: Element 11 and wherein the fluid is a first fluid comprising a first aqueous phase and a first oleaginous phase, and wherein the method further comprises: contacting the second ion selective fiber with a second fluid comprising a second aqueous phase and a second oleaginous phase after exposing the second ion selective fiber to the light; measuring a third color change of the second ion selective fiber in response to contact with the second fluid as a function of time; deriving a second effective time constant for the third color change of the second ion selective fiber in response to contact with the second fluid; and calculating a second concentration of the second aqueous phase in the second fluid based on the second effective time constant and the intrinsic time constant; Element 13: Element 11 and wherein refreshing the second ion selective fiber is conducted while the sensor is in a wellbore penetrating a subterranean formation; Element 14: wherein the fluid is a first fluid, and wherein the method further comprises: refreshing the second ion selective fiber by exposing the second ion selective fiber to a second fluid having a reduced concentration of a chromo-ionophore or an ionophore as compared to the first fluid; Element 15: Element 14 and wherein the first fluid comprises a first aqueous phase and a first oleaginous phase, and wherein the method further comprises: contacting the second ion selective fiber with a second fluid comprising a second aqueous phase and a second oleaginous phase after exposing the second ion selective fiber to the light; measuring a third color change of the second ion selective fiber in response to contact with the second fluid as a function of time; deriving a second effective time constant for the third color change of the second ion selective fiber in response to contact with the second fluid; and calculating a second concentration of the second aqueous phase in the second fluid based on the second effective time constant and the intrinsic time constant; Element 16: Element 14 and wherein refreshing the second ion selective fiber is conducted while the sensor is in a wellbore penetrating a subterranean formation; Element 17: the method further comprising producing the fluid from a subterranean formation via a wellbore penetrating the subterranean formation, wherein the first and second ion selective fibers are portions of a sensor in the wellbore; and Element 18: Element 17 and wherein the subterranean formation comprises a first zone upstream of a second zone; wherein the sensor is a first sensor at a first location along the wellbore that is downstream of the first zone and upstream of the second zone, the $\tau_{\it{eff}}$ is a first $\tau_{\it{eff}}$, and the Y is a first Y, and wherein the method further includes: contacting a second sensor with a fluid, wherein the second sensor is at a second location along the wellbore that is downstream of the first and second zones and comprises a third ion selective fiber that is same as the second ion selective fiber; measuring a third color change of the third ion selective fiber of the second sensor in response to contact with the fluid as a function of time; deriving a second $\tau_{\it{eff}}$ for the third color change; and calculating a second Y of the aqueous phase in the fluid at the third sensor based on the $$Y = \frac{\tau_0}{\tau_{\it{eff}}}$$

and the second $\tau_{\it{eff}}$. Exemplary combinations may include, but are not limited to, Elements 11 and 14 in combination and optionally in further combination with at least one of Elements 12, 13, 15, or 16; Elements 11, 14, and 17 in combination and optionally in further combination with at least one of Elements 12, 13, 15, 16, or 18; Elements 11 and 17 in combination and optionally in further combination with at least one of Elements 12, 13, or 18; Elements 14 and 17 in combination and optionally in further combination with at least one of Elements 15, 16, or 18; Element 10 in combination with any of the foregoing combinations; and Element 10 in combination with one or more of Elements 11-18.

Embodiment C is a system that comprises: a tubular extending from a wellhead into a wellbore penetrating one or more zones of a subterranean formation and containing a fluid comprising an aqueous phase and an oleaginous phase; and at least one sensor in the wellbore and comprising a light source, at least one ion selective fiber configured to contact the fluid, and a detector configured to receive light from the at least one ion selective fiber.

Optionally, Embodiment C may include one or more of the following elements: Element 19: wherein the one or more zones includes a first zone upstream of a second zone and the at least one sensor includes a first sensor is in the wellbore downstream of the first zone and upstream of the second zone and a second sensor is in the wellbore downstream of the first and second zones; Element 20: the system further comprising: a processor communicably coupled to the at least one sensor and configured to receive data from the at least one detector and calculate a water cut (Y) of the aqueous phase in the fluid based on $$Y = \frac{\tau_0}{\tau_{\it{eff}}},$$

where $\tau_0$ is an intrinsic time constant of a first fiber of the at least one ion selective fibers and $\tau_{\it{eff}}$ is effective time constant corresponding to a color change of the first fiber in response to contact with the fluid; and Element 21: wherein the at least one ion selective fiber comprises an outer layer as a diffusion barrier that increases an intrinsic time constant ($\tau_0$) of the at least one ion selective fiber.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating the invention embodiments disclosed herein are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While compositions and methods are described herein in terms of "comprising" various components or steps, the compositions and methods can also "consist essentially of" or "consist of" the various components and steps.

To facilitate a better understanding of the embodiments of the present invention, the following examples of preferred or representative embodiments are given. In no way should the following examples be read to limit, or to define, the scope of the invention.

EXAMPLES

Figure 6:
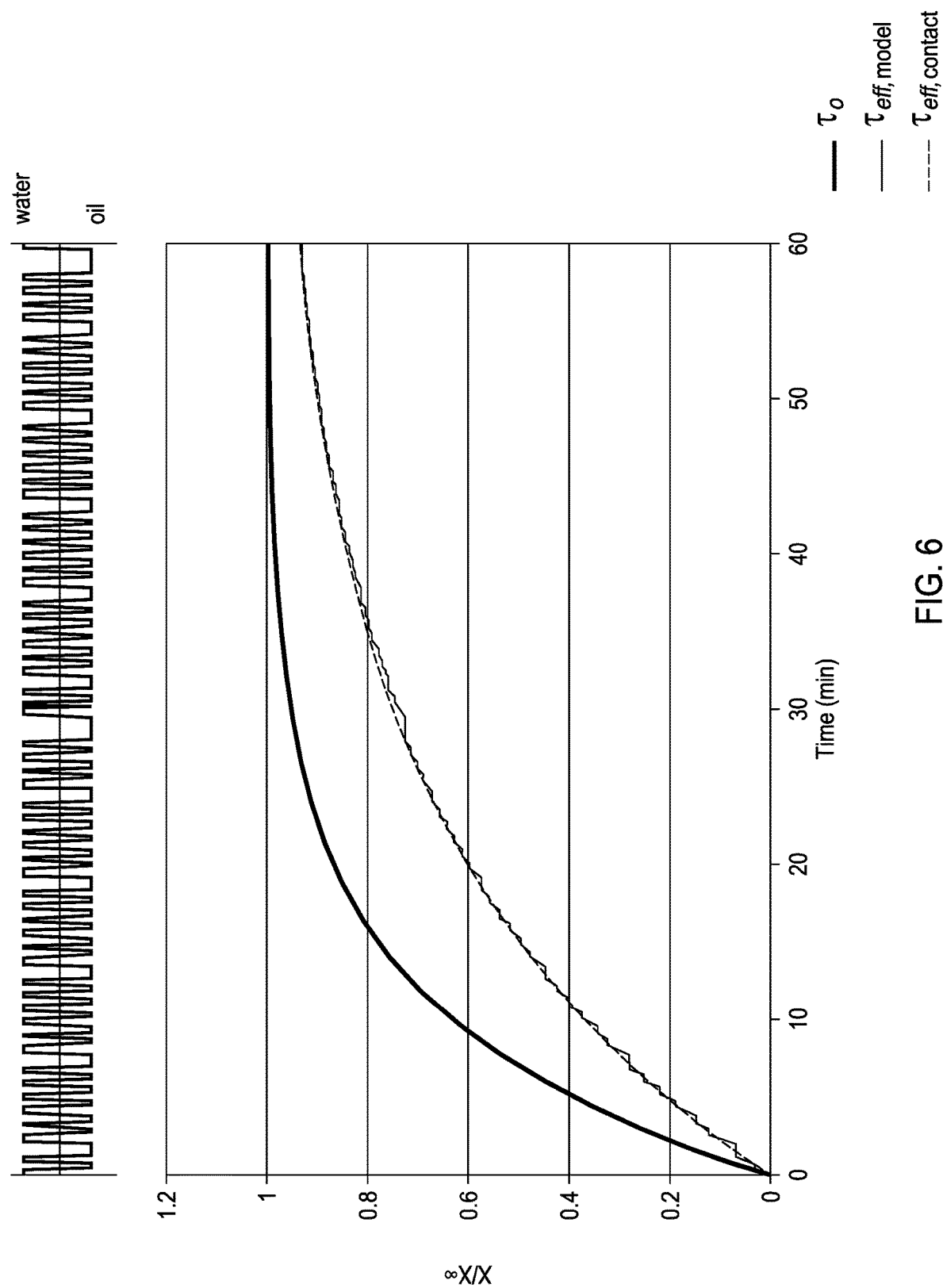
FIG. 6 is a graph plotting the results of a simulated model from the Examples.

Contact between an ion selective fiber having a known $\tau_0$ and a multi-phase fluid were simulated to calculate $\tau_{\it{eff}}$ and Y according to the methods described herein. FIG. 6 is a graph plotting the results of the simulated model. A top plot indicates when the ion selective fiber is in contact with the aqueous phase or the oleaginous phase of the multi-phase fluid. The bottom plot includes plots for the $\tau_0$, the $T_{\it{eff,calc}}$ ($\tau_{\it{eff}}$ calculated by the model), and the $\tau_{\it{eff,contact}}$ ($\tau_{\it{eff}}$ calculated in response to contact with the multi-phase fluid). The plots illustrate that the ion selective fiber changes colors at a slower rate when exposed to the multi-phase fluid (see $\tau_{\textit{eff,contact}}$ plot) than when exposed to a 100% aqueous fluid (see $\tau_0$ plot). Further, the graph illustrates that the $\tau_{\textit{eff,calc}}$ is substantially similar to the $\tau_{\textit{eff,contact}}$, which indicates that the methods described herein may be useful in determining the water cut of multi-phase fluids.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

The invention claimed is:

1. A method comprising:
    flowing a fluid comprising an aqueous phase and an oleaginous phase through a sensor;
    contacting an ion selective fiber positioned in the sensor with the fluid, wherein the ion selective fiber has an intrinsic time constant ($\tau_0$) associated with an intrinsic color change of the ion selective fiber in response to contact with the aqueous phase;
    measuring a color change of the ion selective fiber in response to contact with the fluid as a function of time;
    deriving an effective time constant ($\tau_{\textit{eff}}$) for the color change of the ion selective fiber in response to contact with the fluid; and
    calculating a water cut (Y) in the fluid based on $$Y = \frac{\tau_0}{\tau_{\textit{eff}}},$$

wherein salinity of the aqueous phase at the intrinsic time constant is equal to salinity of the aqueous phase at the effective time constant.

2. The method of claim 1, wherein the ion selective fiber comprises an outer layer as a diffusion barrier that increases $\tau_0$.

3. The method of claim 1, wherein the sensor further comprises a light source and the method further comprises:
    refreshing the ion selective fiber by exposing the ion selective fiber to light emitted from the light source.

4. The method of claim 3, wherein the fluid is a first fluid comprising a first aqueous phase and a first oleaginous phase, and wherein the method further comprises:
    contacting the ion selective fiber with a second fluid comprising a second aqueous phase and a second oleaginous phase after exposing the ion selective fiber to the light;
    measuring a second color change of the ion selective fiber in response to contact with the second fluid as a function of time;
    deriving a second effective time constant for the second color change of the ion selective fiber in response to contact with the second fluid; and
    calculating a second concentration of the second aqueous phase in the second fluid based on the second effective time constant and the intrinsic time constant.

5. The method of claim 1 wherein the fluid is a first fluid, and wherein the method further comprises:
    refreshing the ion selective fiber by exposing the ion selective fiber to a second fluid having a reduced concentration of a chromo-ionophore or an ionophore as compared to the first fluid.

6. The method of claim 5, wherein refreshing the ion selective fiber is conducted while the sensor is in a wellbore penetrating a subterranean formation.

7. The method of claim 1 further comprising:
    producing the fluid from a subterranean formation via a wellbore penetrating the subterranean formation, wherein the sensor is in the wellbore.

8. The method of claim 7, wherein the subterranean formation comprises a first zone upstream of a second zone, and wherein the sensor is a first sensor at a first location along the wellbore downstream of the first zone and upstream of the second zone, the ion selective fiber is a first ion selective fiber, the color change is a first color change, the $\tau_{\textit{eff}}$ is a first $\tau_{\textit{eff}}$, and the Y is a first Y, and wherein the method further includes:
    contacting a second sensor with a fluid, wherein the second sensor is at a second location along the wellbore that is downstream of the first and second zones and comprises a second ion selective fiber that is same as the first ion selective fiber;
    measuring a second color change of the second ion selective fiber of the second sensor in response to contact with the fluid as a function of time;
    deriving a second $\tau_{\textit{eff}}$ for the second color change; and
    calculating a second Y of the aqueous phase in the fluid at the second sensor based on the $$Y = \frac{\tau_0}{\tau_{\textit{eff}}}$$

and the second $\tau_{\textit{eff}}$.

* * * * *